(12) United States Patent
Dal Farra et al.

(10) Patent No.: US 8,809,276 B2
(45) Date of Patent: Aug. 19, 2014

(54) ACTIVATOR PEPTIDES FOR SYNTHESIZING EXTRACELLULAR MATRIX PROTEINS, AND COSMETIC COMPOSITIONS INCLUDING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 13/984,568

(22) PCT Filed: Feb. 17, 2012

(86) PCT No.: PCT/FR2012/000064
§ 371 (c)(1),
(2), (4) Date: Aug. 9, 2013

(87) PCT Pub. No.: WO2012/140331
PCT Pub. Date: Oct. 18, 2012

(65) Prior Publication Data
US 2014/0044655 A1    Feb. 13, 2014

(30) Foreign Application Priority Data

Feb. 18, 2011   (FR) .................................... 11 00497

(51) Int. Cl.
| | | |
|---|---|---|
| *A61K 38/08* | (2006.01) | |
| *C07K 7/00* | (2006.01) | |
| *C07K 7/04* | (2006.01) | |
| *C07K 7/06* | (2006.01) | |
| *A61Q 17/00* | (2006.01) | |
| *A61Q 19/00* | (2006.01) | |
| *A61Q 19/08* | (2006.01) | |
| *A61K 8/64* | (2006.01) | |
| *A61Q 17/04* | (2006.01) | |

(52) U.S. Cl.
CPC . *A61K 8/64* (2013.01); *A61Q 19/00* (2013.01); *A61Q 19/08* (2013.01); *C07K 7/06* (2013.01); *A61K 2800/74* (2013.01); *A61Q 17/04* (2013.01)

USPC ....... 514/18.6; 514/21.6; 514/21.7; 514/21.8; 530/328; 530/329; 530/330

(58) Field of Classification Search
CPC .............. C07K 7/00; C07K 7/04; C07K 7/06; C07K 9/0014; A61K 38/08; A61Q 17/00; A61Q 19/00; A61Q 19/004; A61Q 19/005; A61Q 19/08
USPC .............. 514/18.6, 21.6, 21.7, 21.8; 530/328, 530/329, 330
See application file for complete search history.

(56) References Cited

U.S. PATENT DOCUMENTS

| 4,703,107 A | * | 10/1987 | Monsigny et al. ............ 530/330 |
| 5,837,218 A | * | 11/1998 | Peers et al. .................... 424/1.69 |
| 2007/0054298 A1 | | 3/2007 | Kirshenbaum |

FOREIGN PATENT DOCUMENTS

| FR | 2940971 | | 7/2010 | |
| JP | 56018948 | * | 2/1981 | ............ C07C 103/52 |
| WO | 2007/087131 | | 8/2007 | |

OTHER PUBLICATIONS

Machine translation of JP 56018948, abstract only, (1981), Accessed Jan. 27, 2014.*
Brookes, S. et al., "Contribution of p16[INK4a] to replicative senescence of human fibroblasts," Experimental Cell Research, 298, pp. 549-559 (2004).
International Search Report, International Application No. PCT/FR2012/000064 (mailed May 11, 2012, published Oct. 18, 2012).
Kullmann, W., "Proteases as Catalysts for Enzymic Syntheses of Opioid Peptides," The Journal of Biological Chemistry, vol. 255, No. 17, pp. 8234-8238 (Sep. 10, 1980).

* cited by examiner

*Primary Examiner* — Julie Ha
(74) *Attorney, Agent, or Firm* — Thompson Hine L.L.P.

(57) ABSTRACT

New peptides activating extracellular matrix protein synthesis in the skin, a cosmetic composition that includes such peptides as an active agent, and cosmetic care methods intended to delay or treat cutaneous signs of aging and photoaging by applying such peptides and/or cosmetic compositions are described.

14 Claims, No Drawings

ACTIVATOR PEPTIDES FOR SYNTHESIZING EXTRACELLULAR MATRIX PROTEINS, AND COSMETIC COMPOSITIONS INCLUDING SAME

FIELD OF THE INVENTION

This invention relates to the field of cosmetic and dermatopharmaceutical active agents as well as compositions comprising same.

This invention is intended to provide new peptides activating extracellular matrix protein expression.

The invention also relates to cosmetic compositions comprising such peptides, as active agents, in a physiologically suitable medium.

The invention also relates to the use of such compositions for increasing extracellular matrix protein expression, delaying the appearance of and/or fighting cutaneous signs of aging, and in particular wrinkles, sagging and loss of cutaneous volume and dehydration of the skin, and, finally cosmetic care methods intended to delay the appearance of and/or treat cutaneous signs of aging and photoaging.

BACKGROUND OF THE INVENTION

The skin is a covering organ comprised of a plurality of layers (dermis, dermoepidermal junction, epidermis). The dermis is the tissue supporting the skin and is comprised of water, elastin fibers and collagen fibers (70% of dermal fibers), enveloped in an interstitial matrix of proteoglycans. Fibroblasts are the main cellular component of the dermis and are the source of collagen fiber and elastin fiber synthesis.

Glycosaminoglycans ensure the structuring of collagen and elastin fibrils and the storage of water, owing to their exceptional hygroscopy. Hyaluronic acid is the most abundant glycosaminoglycan in the skin, and the major constituent of the dermis, but is also present around the keratinocytes in the epidermis. The glycosaminoglycan and collagen complexes are major players in skin flexibility and firmness.

The skin, like all of the other organs, is subjected to the complex physiological process of aging. Intrinsic or chronological aging, and extrinsic aging are distinguished. Intrinsic aging is the consequence of a genetically programmed senescence and biochemical alterations due to endogenous factors. In the skin, it is characterized by a slowing of the regeneration of cells and extracellular matrices, leading to dermal and epidermal atrophy, dryness, a reduction in elasticity, and the appearance of fine lines and wrinkles.

As for extrinsic aging, it is due to environmental stresses such as pollution, the sun, diseases, lifestyle habits, etc. Its effects are combined with those of intrinsic aging in areas chronically exposed to these aggressions; this is referred to as photoaging. The main alterations associated with photoaging comprise: the appearance of pigmentary spots, as well as a reduction and disruption of collagen fibers causing wrinkles to appear.

Research to identify the active agents capable of fighting cutaneous aging has led to the market release of numerous more or less effective active agents. However, it remains important to identify new compounds capable of delaying the appearance of or more effectively fighting the cutaneous signs aging. The problem more specifically targeted by the invention is that of identifying new active agents capable of fighting the main cutaneous signs of aging located at the extracellular matrix.

DESCRIPTION OF THE INVENTION

The inventors have demonstrated that peptides with the following general formula (I):

$$R_1\text{-}(AA)_n\text{-}X_1\text{-}Pro\text{-}X_2\text{-}Gly\text{-}Pro\text{-}X_3\text{—}X_4\text{-}(AA)_p\text{-}R_2$$

were good extracellular matrix protein synthesis activators. Consequently, these peptides are suitable for fighting skin aging and photoaging.

The peptides according to the invention are characterized in that they:
increase the expression of type-I and type-III collagens
increase the expression of fibronectin,
increase the expression of hyaluronic acid,
reduce the signs of senescence of fibroblasts "Peptide or active agent activating extracellular matrix proteins" means any peptide of general formula (I) capable of increasing the amount of collagen, fibronectin and hyaluronic acid present in the cell, or secreted either by increasing protein synthesis by direct or indirect modulation of gene expression or by other biological processes such as protein stabilization or stabilization of messenger RNA transcriptions.

"Signs of senescence of fibroblasts" means the expression profile of biochemical markers associated with the cellular senescence phenotype.

Skin refers to all of the covering tissue constituting the skin, the mucous membranes and the skin appendages, including hair, eyelashes and eyebrows.

Thus, the invention relates firstly to a peptide of general formula (I)

$$R_1\text{-}(AA)_n\text{-}X_1\text{-}Pro\text{-}X_2\text{-}Gly\text{-}Pro\text{-}X_3\text{—}X_4\text{-}(AA)_p\text{-}R_2$$

Wherein
$X_1$ represents glycine or alanine or valine,
$X_2$ represents glycine or alanine or valine,
$X_3$ represents asparagine or lysine or glutamine or no amino acid,
$X_4$ represents phenylalanine or tyrosine or no amino acid,
AA represents any amino acid and n and p are integers between 0 and 2,
$R_1$ represents the primary amine function of the N-terminal amino acid, —$NH_2$, wherein one of the two hydrogen atoms can be substituted either by a saturated or unsaturated $C_1$ to $C_{30}$ alkyl chain, or by an acyl-type group (R—CO—) wherein the radical R is a saturated or unsaturated $C_1$ to $C_{30}$ alkyl chain and preferably a methyl, or by an aromatic group of the benzoyl, tosyl or benzyloxycarbonyl type,
$R_2$ represents the hydroxyl group of the carboxyl function of the C-terminal amino acid, —OH, wherein the hydrogen atom can be substituted by a $C_1$ to $C_{30}$ alkyl chain, or an $NH_2$, NHY or NYY group, wherein Y represents a $C_1$ to $C_4$ alkyl chain,
said sequence of general formula (I) consisting of 5 to 11 amino acid residues and capable of being in the form of salts.

According to a very particularly preferred embodiment of the invention, the peptide is of sequence:

```
(SEQ ID NO: 1):
Ala-Pro-Ala-Gly-Pro-NH2

(SEQ ID NO: 2):
Val-Pro-Ala-Gly-Pro-NH2

(SEQ ID NO: 3):
Val-Pro-Gly-Gly-Pro-NH2
```

-continued (SEQ ID NO: 5):
Gly-Pro-Ala-Gly-Pro-NH$_2$ or (SEQ ID NO: 6):
Lys-Gly-Ala-Pro-Gly-GLy-Pro-Asn-Tyr-NH$_2$.

According to a particularly beneficial embodiment, the peptide corresponds to sequence SEQ ID NO: 4.

According to another particularly beneficial embodiment, the peptide corresponds to sequence SEQ ID NO: 5.

The amino acids, constituting the peptide according to the invention and designated under the terms AA, can be in an L- and D-isomeric configuration. Preferably, the amino acids are in L form.

The term "peptide" refers to a chain of two or more amino acids bound to one another by peptide bonds.

"Peptide" also refers to the natural or synthetic peptide of the invention as described above, or at least one of its fragments, whether it is obtained by proteolysis or synthetically, or any natural or synthetic peptide of which the sequence consists entirely or partially of the sequence of the peptide described above.

To improve resistance to degradation, it may be necessary to use a protected form of the peptide according to the invention. It is possible to protect the primary amine function of the N-terminal amino acid, either by substitution with an $R_1$ group of the acyl type (R—CO—) in which the radical R is a saturated or unsaturated $C_1$ to $C_{30}$ alkyl chain, preferably of the methyl type, or by a substitution with an aromatic group of the benzoyl, tosyl, or benzyloxycarbonyl type.

Preferably, the carboxyl function of the C-terminal amino acid is protected by a substitution with an $R_2$ group of the $C_1$ to $C_{30}$ alkyl chain type, or an NH$_2$, NHY or NYY group with Y representing a $C_1$ to $C_4$ alkyl chain.

The peptide according to the invention, of sequence SEQ ID NO: 1 to SEQ ID NO: 6, can be protected at the N-terminal or C-terminal end or at both ends.

The peptide of general formula (I) according to the invention can be obtained either by classic chemical synthesis (in the solid phase or in the liquid homogeneous phase), or by enzymatic synthesis (Kullman et al. J. Biol. Chem., 1980, vol. 225, p. 8234) from constituent amino acids.

The peptide according to the invention can be of natural or synthetic origin. Preferably, according to the invention, the peptide is of synthetic origin, obtained by chemical synthesis.

According to the invention, the active agent can be a single peptide or a mixture of peptides.

The peptide according to the invention is advantageously solubilized in one or more physiologically suitable solvents, such as water, glycerol, ethanol, propanediol, butylene glycol, dipropylene glycol, the ethoxylated or propoxylated diglycols, the cyclic polyols or any mixture of these solvents.

"Physiologically suitable" means solvents or media that are suitable for use in contact with the human skin or skin appendages, without the risk of toxicity, intolerance, instability, allergic response or other adverse effects.

The diluted peptide is then sterilized by sterile filtration.

After this dilution step, the peptide can be encapsulated or contained in a cosmetic vector such as liposomes or any other microcapsule used in the cosmetic field or adsorbed on powdery organic polymers, mineral carriers such as talcs and bentonites, and more generally solubilized in, or bonded to, any physiologically suitable vector.

The invention relates secondly to a cosmetic composition comprising, in a physiologically suitable medium, a peptide of general formula (I), as an active agent activating extracellular matrix protein synthesis in the skin.

According to an advantageous embodiment of the invention, the active agent is present in the compositions at a concentration of between 0.0005 and 500 mg/kg, and preferably between 0.01 and 5 mg/kg with respect to the total weight of the final composition.

This range of concentrations represents the quantity of active agent necessary for obtaining the desired molecular effect, namely, activating the expression of type-I and type-III collagens, fibronectin and hyaluronic acid.

Preferably, the composition according to the invention is in a form suitable for topical application comprising a medium physiologically suitable for the skin.

"Topical application" refers to the application or spreading of the active agent according to the invention, or a composition containing it, on the surface of the skin.

These compositions may in particular be in the form of an aqueous, hydro-alcoholic or oily solution; an oil-in-water or a water-in-oil emulsion or multiple emulsions, aqueous or anhydrous gel, colloid. These compositions can also be in the form of creams, suspensions, or powders, suitable for application on the skin, mucous membranes, lips and/or skin appendages. These compositions may be more or less fluid and have the appearance of a cream, a lotion, a milk, a serum, a pomade, a cream, a paste or a foam. They may also be in solid form, such as a stick, or be applied to the skin in aerosol form. They may be used as a care product and/or as a make-up product for the skin.

All of these compositions comprise, in addition, any additive commonly used in the field of use envisaged as well as the adjuvant necessary for their formulation, such as co-solvents (ethanol, glycerol, benzyl alcohol, humectant, . . . ), thickening agents, diluents, emulsifiers, antioxidants, coloring agents, sunscreens, pigments, fillers, preservatives, fragrances, odor absorbents, essential oils, trace elements, essential fatty acids, surfactants, film-forming polymers, chemical or mineral filters, hydrating agents or thermal water, and so on. It is possible, for example, to cite water-soluble polymers of a natural type, such as polysaccharides, or polypeptides, cellulosic derivatives of the methylcellulose or hydroxypropyl cellulose type, or synthetic polymers, poloxamers, carbomers, siloxanes, PVA or PVP, and in particular polymers sold by the ISP company.

In any case, a person skilled in the art will make sure that these adjuvants as well as their proportions are chosen so as not to counteract the advantageous properties sought in the composition according to the invention. These adjuvants may, for example, be present in concentrations ranging from 0.01 to 20% of the total weight of the composition. When the composition of the invention is an emulsion, the fatty phase may represent 5 to 80% by weight and preferably 5 to 50% by weight with respect to the total weight of the composition. The emulsifiers and co-emulsifiers used in the composition will be chosen from those conventionally used in the field considered. For example, they can be used in a proportion ranging from 0.3 to 30% by weight, with respect to the total weight of the composition.

Of course, the active agent according to the invention can be used alone or in association with other active agents.

Advantageously, the compositions that can be used according to the invention contain, in addition, at least one other active agent intended to reinforce the action of the active agent according to the invention, in the field of preventing and improving skin signs of aging, or another active agent making it possible to expand the range of properties of the composition considered.

It is possible to cite, in a non-limiting manner, the following classes of ingredients: regenerating, anti-aging, antiwrinkle, soothing, anti-free radical, anti-glycation, hydrating, antibacterial, antifungal, keratolytic, muscle relaxing, exfoliating, and firming agents, agents stimulating the synthesis of dermal macromolecules or energy metabolism or microcirculation or nail or hair growth, agents modulating differentiation or pigmentation of the epidermis, metalloproteinase-inhibiting agents or sunscreen and sun filters.

In a particular embodiment of the invention, the composition according to the invention will also comprise, aside from the peptide according to the invention,

- at least one cytochrome c-activating compound, and/or
- at least one hydrating compound, such as an aquaporin-activating compound, and/or
- at least one sirtuin-activating compound, and/or
- at least one cell adhesion-increasing compound, and/or
- at least one compound that increases the production of matrix proteins such as collagen, fibronectin, laminin, glycosaminoglycans, and/or
- at least one proteasome activity-modulating compound, and/or
- at least one circadian rhythm-modulating compound, and/or
- at least one HSP protein-modulating compound, and/or
- at least one cellular energy-increasing compound, and/or
- at least one skin pigmentation-modulating compound, and/or
- at least one coenzyme Q10-activating compound, and/or
- at least one compound improving the barrier function, such as a transglutaminase or HMG-CoA reductase-activating compound, and/or
- at least one mitochondria-protecting compound.

Said above compounds may be of natural origin, such as peptide hydrolysates of plants, or of synthetic origin, such as peptides.

Independently of their functions, the other active agents associated with the active agent according to the invention in the composition may have very diverse chemical structures. It is possible to cite, in a non-limiting manner, peptides, vitamin C and derivatives thereof, B-group vitamins, DHEA (dihydroepiandrosterone), phytosterols, salicylic acid and derivatives thereof, retinoids, flavonoids, sugar amines, azoles, metal salts, peptide extracts of plant origin or polymers.

The invention relates thirdly to the use of a cosmetic composition, comprising the peptide of general formula (I) as an active agent, for increasing extracellular matrix protein synthesis by the skin cells.

More specifically, the peptide according to the invention is used to increase the synthesis of collagen I and III and fibronectin by the fibroblasts of human skin.

According to this particular embodiment of the invention, the peptide of general formula (I) is used to increase the density of the dermis, and therefore the firmness of the skin, to delay or reduce sagging of facial lines, loss of volume of the dermis, thinning of the skin, atonia, fine lines, deep wrinkles and dermal atrophy.

The invention relates fourthly to the use of a cosmetic composition, comprising the peptide of general formula (I) as an active agent for increasing the expression of hyaluronic acid both by fibroblasts and keratinocytes.

According to this particular embodiment of the invention, the peptide of general formula (I) is used to increase the capacity of all of the layers of the skin for retaining water and delaying or reducing skin dehydration related to aging.

The invention relates fifthly to the use of a cosmetic composition, comprising the peptide of general formula (I) as an active agent for delaying the appearance of or reducing senescence of skin cells.

The phrase "delaying the appearance of or reducing senescence of dermis cells" means that, according to this advantageous aspect of the invention, the peptide of the invention reduces the expression of senescence markers in human fibroblasts in which senescence has been induced by extinction of the FOXO3a gene.

The invention relates sixthly to a cosmetic care method intended to delay and/or treat cutaneous signs of aging and photoaging, characterized in that a composition according to the invention is applied topically to the skin to be treated.

"Cutaneous signs of aging" refers to all changes in the external appearance of the skin and skin appendages due to aging, such as, for example, thinning of the skin, sagging, loss of hydration and atonia, deep wrinkles and fine lines, loss of firmness and tone, dermal atrophy or any other internal degradation of the skin resulting from exposure to UV radiation.

Other advantages and features of the invention will become clearer in view of the following examples provided for illustrative and non-limiting purposes.

Example 1

Demonstration of the Activating Effect of the Peptides SEQ ID NO: 4 and NO: 5 on the Expression of Collagen I, Collagen III, Pro-Collagen, Fibronectin and Hyaluronic Acid in Human Fibroblasts The objective of this study is to determine the influence of the peptides SEQ ID NO: 4 and NO: 5 and the peptide SEQ ID NO: 4 on the expression of the following extracellular matrix proteins: collagen I, collagen III, pro-collagen, fibronectin and hyaluronic acid in human fibroblasts. For this, specific labelings were performed on normal human fibroblast cultures obtained from the dermis.

Specific Labeling Protocol:

Human fibroblasts in culture are treated with the peptide SEQ ID NO: 5 or the peptide SEQ ID NO: 4 at a final concentration of 0.5%, 1% and/or 3% (based on a stock solution at 40 mg/kg), for 24, 48 and/or 72 hours. The cells are then washed, fixed with cold methanol for 4 minutes at 4° C. (for the collagen I, collagen III and hyaluronic acid labelings) or with formaldehyde at 3.7% for 10 minutes at room temperature (for the pro-collagen and fibronectin labelings). The cells are incubated in the presence of a specific rabbit collagen I polyclonal antibody (Rockland, Ref: 600-401-103-0.5), a specific rabbit collagen III polyclonal antibody (Rockland, Ref: 600-401-105-0.5), a specific rat pro-collagen polyclonal antibody (Millipore, Ref: MAB1912), a specific rabbit fibronectin polyclonal antibody (Sigma, Ref: F-3648), then an anti-rabbit secondary antibody coupled with a fluorochrome (Invitrogen, Ref: A21206) or anti-rat coupled with a fluorochrome (Invitrogen, A11006). For the labeling of hyaluronic acid, the cells are incubated in the presence of a specific biotinylated protein (Coger, Ref: 4007631A), then in the presence of streptavidin coupled with a fluorochrome (Invitrogen, Ref: S32354). The cells are then examined under the epifluorescence microscope (Nikon Eclipse E600 microscope).

Results:

Under all of the conditions tested, more intense fluorescence is observed in the fibroblasts treated by the peptide SEQ ID NO: 5 or the peptide SEQ ID NO: 4 than under the control conditions.

Conclusions:

The peptides SEQ ID NO: 5 and SEQ ID NO: 4 stimulate the expression of collagen I, collagen III, pro-collagen, fibronectin and hyaluronic acid by the human dermal fibroblasts.

Example 2

Demonstration of the Activating Effect of the Peptide SEQ ID NO: 5 on the Expression of Collagen I, Collagen III, Pro-Collagen and Hyaluronic Acid in Skin Biopsies The objective of this study is to determine the influence of the peptide SEQ ID NO: 5 on the expression of the following extracellular matrix proteins: collagen I, collagen III, pro-collagen, fibronectin and hyaluronic acid in the human skin. For this, specific labelings were performed on human skin samples cultivated ex vivo.

Protocol:

Human skin samples are placed in culture at the air/liquid interface. The peptide SEQ ID NO: 5 is applied topically on the samples at final concentrations of 0.5%, 1% or 3%, (using a stock solution at 40 mg/kg) then the samples are incubated for 24, 48 and/or 72 hours at 37° C.

These skin samples are then fixed with formaldehyde then embedded in paraffin or fixed and embedded in OCT then frozen at −20° C. Sections with a thickness of 4 µm are then produced (6 µm for cold sections).

The labelings of the collagen I and the collagen III, on the samples embedded in paraffin, are performed after unmasking specific sites. The immunolabelings are performed using a specific rabbit collagen I polyclonal antibody (Rockland, Ref: 600-401-103-0.5), a specific rabbit collagen III polyclonal antibody (Rockland, Ref: 600-401-105-0.5), then an anti-rabbit secondary antibody coupled with a fluorochrome (Invitrogen, Ref: A21206). For labeling of the hyaluronic acid, the cells are incubated in the presence of a specific biotinylated protein (Coger, Ref: 4007631A), then in the presence of streptavidin coupled with a fluorochrome (Invitrogen, Ref: S32354).

The immunolabeling of the pro-collagen, on the samples embedded in OCT, is performed after fixing for 10 minutes with cold acetone. The immunolabeling is performed using a specific rat pro-collagen polyclonal antibody (Millipore, Ref: MAB 1912) then an anti-rat secondary antibody, coupled with a fluorescent marker (Invitrogen, A11006).

The cells are then examined under the epifluorescence microscope (Nikon Eclipse E600 microscope).

Results:

The microscopic observations show a more intense fluorescence at the dermis of the skin samples treated with the peptide SEQ ID NO: 5. In the case of the immunolabeling of the hyaluronic acid, an increase in fluorescence is also observed at the epidermis of the skin samples treated with the peptide SEQ ID NO: 5.

Conclusions:

The peptide SEQ ID NO: 5 stimulates the expression of collagen I, collagen III, pro-collagen in the dermis and stimulates the expression of hyaluronic acid in the human dermis and epidermis.

Example 3

Demonstration of the Activating Effect of the Peptide SEQ ID NO: 5 on the Expression of Collagen I Messenger RNAs by Real-Time PCR The objective of this study is to determine the influence of the peptide SEQ ID NO: 5 on the expression of collagen I messenger RNAs in the human fibroblasts. For this, the expression of collagen I was studied by real-time PCR.

Protocol:

Human fibroblasts in culture are treated with the peptide SEQ ID NO: 5 at final concentrations of 0.5% and 1% (using a stock solution at 40 mg/kg) for 24, 48 and 72 hours. The total RNAs are extracted using an extraction kit (QIAGEN), then reverse transcribed with a specific kit containing RNase inhibitors (Applied Biosystems). A real-time PCR is performed in a thermocycler using a specific Collagen I TaqMan Gene Expression Assay (Applied Biosystem, Hs99999901_s1) and a specific 18S TaqMan Gene Expression Assay used as an endogenous control (Applied Biosystem, Hs00164004_m1). The relative quantification of the expression of the Collagen I messenger RNAs is performed by the comparative Ct method (the Ct, the threshold cycle, is the intersection between the amplification curve and the threshold line).

Results/Conclusion:

The peptide SEQ ID NO: 5 stimulates the expression of Collagen I messenger RNAs in human fibroblasts.

Example 4

Study of the Expression of the Senescence Marker P16 in the Presence of the Peptide SEQ ID NO: 5

The objective of this study is to determine the influence of the peptide SEQ ID NO: 5 on the expression of P16, a protein of which the expression in the skin increases with age. P16 is a protein involved in the negative regulation of the cellular cycle, which has been described as a reliable marker of cellular senescence (Brookes S. et al. Experimental Cell Research 298, 2004).

Protocol:

Human fibroblasts in culture are treated with the peptide SEQ ID NO: 5 at final concentrations of 0.5% and 1% (using a stock solution at 40 mg/kg) for 48 hours. The cells are prepared according to the Shandon Cytoblock® Cell preparation system kit (Thermo Scientific, Ref: 7401150).

The cells are then fixed with formaldehyde then embedded in paraffin. Sections of 4 µm are then produced. The labeling of p16 on the cells embedded in paraffin is performed after unmasking the specific sites. The immunolabelings are performed using a specific mouse p16 polyclonal antibody (Santa-Cruz, Ref: sc-81157), then an anti-mouse secondary antibody coupled with a fluorochrome (Invitrogen, Ref: A21202). The cells are then examined under the epifluorescence microscope (Nikon Eclipse E600 microscope).

Results:

The microscopic observations show less intense nuclear fluorescence in the cells treated with the peptide SEQ ID NO: 5.

Conclusions:

The peptide SEQ ID NO: 5 reduces the expression of the p16 senescence marker in human fibroblasts.

Example 5

Demonstration of the Reversal of Cellular Senescence Induced in Fibroblasts, by the Peptide SEQ ID NO: 5

The objective of this study is to determine the influence of the peptide SEQ ID NO: 5 on senescent fibroblasts, of which the senescence has been induced by the extinction of the FOXO3a gene. These cells overexpress beta-galactosidase, in relation to their senescent state.

FOXO3a is a Forkhead transcription factor involved in cell longevity. In the skin, the negative regulation of FOXO3a accelerates the senescence of normal human fibroblasts (Hyun Kyoung K. et al. J. of Gerontol., 2005, vol. 60A n° 1, pages 4-9). This property was used to advantage to induce senescence in human fibroblasts by blocking FOXO3a expression by a specific interfering RNA (siRNA).

Protocol:

Human fibroblasts in culture are rendered senescent by treatment with a specific siRNA of FOXO3a at a final concentration of 25 nM using the Lipofectamine™ RNAiMAX (Invitrogen, Ref: 13778-075) transfection technique. Untreated controls are produced. The fibroblasts are treated in parallel by the peptide SEQ ID NO: 5 at a final concentration of 1% (using a stock solution at 40 mg/kg) for 48 hours.

The cells are rinsed and fixed in a fixation buffer (0.2% glutaraldehyde, 2% formaldehyde). The cells are then incubated at 37° C. without CO2 for 24 hours with an X-Gal solution at 1 mg/mL in 40 mM of citric acid/phosphate (pH 6), 5 mM K3FeCN6, 5 mM K4FeCN6, 150 mM NaCl and 2 mM MgCl2. The cells are then examined under a white-light microscope (Nikon Eclipse E600 microscope).

Results:

The senescent cells having a specific β-galactosidase activity are stained blue. The cells treated with the specific siRNA of FOXO3a show an increase in the β-galactosidase activity related to the induction of senescence, involving an increase in the number of cells stained blue. The cells treated with the specific siRNAs of FOXO3a and the peptide SEQ ID NO: 5 at 1% show a decrease in the β-galactosidase activity, involving a decrease in the number of cells stained blue.

Conclusion:

The peptide SEQ ID NO: 5 is capable of reducing the senescence phenotype induced in human fibroblasts.

Example 6

Preparation of Compositions

1-Anti-Aging Facial Cream:

| Trade names | INCI names | Weight % |
|---|---|---|
| Phase A | | |
| MONTANOV ™ 68 | Cetearyl Alcohol (and) Cetearyl Glucoside | 6.00 |
| Squalane | Squalane | 3.00 |
| ISP BonjourRefined shea butter | Butyrospermum Parkii (Shea Butter) | 2.00 |
| WAGLINOL ™ 250 | Cetearyl Ethylhexanoate | 3.00 |
| AMERCHOL ™ L-101 | Mineral Oil (and) Lanolin Alcohol | 2.00 |
| SI-TEC ™ DM 350 | Dimethicone | 1.50 |
| BHT | BHT | 0.01 |
| Coenzyme Q10 | Ubiquinone | 0.10 |
| Phase B | | |
| Avocado oil | Persea Gratissima (Avocado) Oil | 1.25 |
| OPTIPHEN ™ | Phenoxyethanol (and) Caprylyl Clycol | 1 |
| Phase C | | |
| Demineralized water | Aqua (Water) | qs |
| Butylene Glycol | Butylene Glycol | 2.00 |
| GLUCAM ™ E10 | Methyl Gluceth-10 | 1.00 |
| Allantoin | Allantoin | 0.15 |
| Carbopol Ultrez 10 | Carbomer | 0.20 |
| Phase D | | |
| TEA | Triethanolamine | 0.18 |
| Phase E | | |
| Peptide SEQ ID NO: 5 | | 3 mg/kg |
| GP4G | Water (and) Artemia Extract | 1.50 |
| COLLAXYL ™ | Water (and) Butylene Glycol (and) Hexapeptide-9 | 3.00 |
| Phase F | | |
| Fragrance | Fragrance | qs |
| Coloring agent | | qs |

Prepare and melt phase A at 65-70° C. Heat phase C at 65-70° C. Phase B is added to phase A just before emulsifying A in C. At around 45° C., the carbomer is neutralized by addition of phase D. At around 30° C., phase E is then added under light stirring and the cooling is continued until reaching 25° C. Phase F is then added if desired.

Applicants incorporate by reference the material contained in the accompanying computer readable Sequence Listing entitled "11-150 SEQ Listing ST25.txt", which was created on Apr. 29, 2014, and is 1,608 bytes in size.

The invention claimed is:

1. A peptide consisting of a peptide sequence:

```
(SEQ ID NO: 1):
Ala-Pro-Ala-Gly-Pro-NH2, (SEQ ID NO: 2):
Val-Pro-Ala-Gly-Pro-NH2, (SEQ ID NO: 3):
Val-Pro-Gly-Gly-Pro-NH2, (SEQ ID NO: 5):
Gly-Pro-Ala-Gly-Pro-NH2,
and (SEQ ID NO: 6):
Lys-Gly-Ala-Pro-Gly-Gly-Pro-Asn-Tyr-NH2.
```

2. The peptide of claim 1, wherein the peptide is solubilized in one or more physiologically acceptable solvents selected from the group consisting of water, glycerol, ethanol, propanediol, butylene glycol, dipropylene glycol, the ethoxylated or propoxylated diglycols, the cyclic polyols, and mixtures of these solvents.

3. A cosmetic composition comprising:
in a physiologically acceptable medium, a peptide consisting of at least one of the following peptide sequences:

```
(SEQ ID NO: 1):
Ala-Pro-Ala-Gly-Pro-NH2, (SEQ ID NO: 2):
Val-Pro-Ala-Gly-Pro, (SEQ ID NO: 3):
Val-Pro-Gly-Gly-Pro-NH2, (SEQ ID NO: 5):
Gly-Pro-Ala-Gly-Pro-NH2,
and (SEQ ID NO: 6):
Lys-Gly-Ala-Pro-Gly-Gly-Pro-Asn-Tyr-NH2,
``` as an active agent activating extracellular matrix protein synthesis in the skin.

4. The composition of claim 3, wherein said peptide is present at a concentration of between 0.0005 and 500 mg/kg with respect to the total weight of the final composition.

5. The composition of claim 3, wherein the composition is a topical composition comprising a delivery vehicle selected from the group consisting of an aqueous, hydro-alcoholic or oily solution; an oil-in-water or a water-in-oil emulsion or multiple emulsions; aqueous or anhydrous gel, colloid, cream, suspension, powder, lotion, milk, serum, pomade, paste, foam, aerosol or stick.

6. The composition of claim 3, further comprising at least one other active agent selected from the group consisting of vitamin C, B-group vitamins, dehydroepiandrosterone (DHEA), phytosterols, salicylic acid, retinoids, flavonoids, sugar amines, azoles, metal salts, and peptide extracts of plant origin.

7. The peptide of claim 1, wherein the peptide is the sequence SEQ ID NO: 5.

8. The composition of claim 4, wherein said peptide is present at a concentration of between 0.01 and 5 mg/kg with respect to the total weight of the final composition.

9. A method for cosmetic treatment of skin, the method comprising:
applying a composition comprising:
one or more peptides consisting of a peptide sequence selected from the group consisting of:

```
(SEQ ID NO: 1):
Ala-Pro-Ala-Gly-Pro-NH2, (SEQ ID NO: 2):
Val-Pro-Ala-Gly-Pro-NH2, (SEQ ID NO: 3):
Val-Pro-Gly-Gly-Pro-NH2, (SEQ ID NO: 5):
Gly-Pro-Ala-Gly-Pro-NH2,
and (SEQ ID NO: 6):
Lys-Gly-Ala-Pro-Gly-Gly-Pro-Asn-Tyr-NH2,
``` and a physiologically acceptable medium.

10. The method of claim 9, wherein applying the composition includes applying an effective amount for increasing the synthesis of type-I and type-III collagens and fibronectin by the fibroblasts.

11. The method of claim 9, wherein applying the composition includes applying an effective amount for increasing the expression of hyaluronic acid by skin fibroblasts and keratinocytes.

12. The method of claim 9, wherein applying the composition includes applying an effective amount for delaying the appearance of or reduces senescence of skin cells.

13. The method of claim 9, wherein applying includes topically applying the composition to the skin.

14. The method of claim 9, wherein applying the composition includes applying an effective amount for treating cutaneous signs of aging and photoaging.

* * * * *

UNITED STATES PATENT AND TRADEMARK OFFICE
CERTIFICATE OF CORRECTION

Page 1 of 1

PATENT NO.           : 8,809,276 B2
APPLICATION NO.      : 13/984568
DATED                : August 19, 2014
INVENTOR(S)          : Claude Dal Farra, Nouha Domloge and Jean-Marie Botto It is certified that error appears in the above-identified patent and that said Letters Patent is hereby corrected as shown below:

In the Claims

In Claim 1, at Column 13, Lines 23-24, it reads:

"(SEQ ID NO: 5):
Gly-Pro-Ala-Gly-Pro-NH$_2$, and"

It should read:

-- (SEQ ID NO: 5):
Gly-Pro-Ala-Gly-Pro-NH$_2$, or --

Signed and Sealed this
Twenty-third Day of December, 2014

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION
```

```
<400> SEQUENCE: 1

Ala Pro Ala Gly Pro
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 2

Val Pro Ala Gly Pro
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 3

Val Pro Gly Gly Pro
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Gly Pro Ala Gly Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 5

Gly Pro Ala Gly Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (9)..(9)
<223> OTHER INFORMATION: AMIDATION

<400> SEQUENCE: 6

Lys Gly Ala Pro Gly Gly Pro Asn Tyr
1               5
```